US00PP29264P3

(12) United States Plant Patent
Kordes

(10) Patent No.: US PP29,264 P3
(45) Date of Patent: May 1, 2018

(54) FLORIBUNDA ROSE PLANT NAMED 'KORFORST750'

(50) Latin Name: *Rosa hybrida*
Varietal Denomination: KORforst750

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 51 days.

(21) Appl. No.: 14/999,480

(22) Filed: May 12, 2016

(65) Prior Publication Data

US 2017/0332526 P1 Nov. 16, 2017

(51) Int. Cl.
*A01H 5/02* (2018.01)

(52) U.S. Cl.
USPC ..... Plt./146
CPC ..... *A01H 5/0222* (2013.01)

(58) Field of Classification Search
USPC ..... Plt./146
See application file for complete search history.

*Primary Examiner* — Keith O Robinson
(74) *Attorney, Agent, or Firm* — Samuel R. McCoy, Jr.

(57) ABSTRACT

'KORforst750' is a new and distinct variety of *Rosa hybrida* which is characterized by the combination of a bushy growth habit, a vigorous rate of growth, high resistance to common rose diseases, and panicles bearing three to six copper-yellow flowers. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORforst750'.

STATEMENT REGARDING PRIOR DISCLOSURES BY THE INVENTOR UNDER 37 C.F.R. 1.77(B)(6)

The first public disclosure of the claimed plant was made by the breeder in a press release on Jun. 29, 2015. 'KORforst750' was not publically available or sold prior to one year before the date of the instant application.

BACKGROUND OF THE INVENTION

Parentage: The *Rosa hybrida* variety 'KORforst750' is the result of a controlled cross-pollination breeding program carried out by the inventor in Klein Offenseth-Sparrieshoop, Germany. The objective of the said breeding program was to create a new and distinct rose plant with unique qualities, such as:

1. Uniform growth and flowering; and
2. Abundant, recurrent copper-yellow flowers; and
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORforst750' from all other varieties known to the inventor.

'KORforst750' is a seedling selection which resulted from the controlled pollination of *Rosa hybrida* 'INTERflocu' (unpatented), the seed parent, and an unnamed *Rosa hybrida* seedling developed and owned by the same inventor, the pollen parent, during the summer of 2003. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2004 from the seedling beds due to its superior characteristics and asexually propagated for further evaluation. This new and distinctive rose variety was given the name 'KORforst750'.

Asexual Reproduction: 'KORforst750' was first asexually propagated by bud grafting in July of 2004 at the inventor's nursery in Klein Offenseth-Sparrieshoop, Germany. Subsequently, 'KORforst750' has been successfully propagated by stem cuttings and bud grafting in Jackson County, Oreg. These initial and other subsequent propagations conducted in controlled environments demonstrate that 'KORforst750' reproduces true to type in successive generations of asexual reproduction.

SUMMARY OF THE INVENTION

The following characteristics have been repeatedly observed and represent the distinguishing characteristics of the new *Rosa hybrida* cultivar 'KORforst750'. These traits, in combination, distinguish 'KORforst750' as a new and distinct cultivar.

1. *Rosa hybrida* 'KORforst750' exhibits a vigorous growth rate and bushy habit; and
2. *Rosa hybrida* 'KORforst750' exhibits high resistance to rust, black spot disease, *Botrytis* and powdery mildew; and
3. *Rosa hybrida* 'KORforst750' exhibits panicles of 3 to 6 copper-yellow flowers held upright to slightly pendant; and
4. *Rosa hybrida* 'KORforst750' exhibits double flowers of small size for a floribunda rose.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORforst750', taken from a two year old plant.

DETAILED BOTANICAL DESCRIPTION

The following is a detailed botanical description of a new and distinct variety of *Rosa hybrida* known as 'KORforst750', based upon observations made in October of 2015 from two year old, field-grown plants in Jackson County, Oreg. Those skilled in the art will appreciate that certain characteristics will vary with older or, conversely, with younger plants. 'KORforst750' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2001 edition except where common terms of color are used.

A botanical description of 'KORforst750' and comparisons with the parents and closest known comparator variety of *Rosa hybrida* are provided below.

General plant description:

*Growth rate.*—Vigorous.

*Growth habit.*—Bushy.

*Mature dimensions.*—120 cm tall and 70 cm wide, on average.

*Cold hardiness.*—Grown successfully in USDA Hardiness Zones 6.

*Propagation.*—Stem cuttings and bud grafting.

*Disease resistance.*—Highly resistant to powdery mildew (*Sphaerotheca pannosa*), blackspot (*Diplocarpon rosae*), rust (*Phragmidium* sp.) and *Botrytis* diseases under normal growing conditions in Jackson County, Oreg.

Root system: Moderately branched, fibrous root system with roots evenly distributed throughout the soil profile, from shallow to deep.

Stems:

*Stem color.*—Young stems are Yellow-Green Group 146C; mature stems are Yellow-Green Group 146D.

*Anthocyanin intonations.*—Intonations of Greyed-Red Group 182B are present on young stems.

*Stem surface texture.*—Both young and mature stems are smooth.

*Stem dimensions.*—Typical mature stems are approximately 50 cm long and 5 mm in diameter.

*Prickles.*—Incidence — Typically 8 prickles per 10 cm of stem, on average. Size — Average length is 10 mm long. Immature prickle color — Greyed-Purple Group 184B. Mature prickle color — Greyed-Orange Group 174D, with anthocyanin intonations of Greyed-Purple Group 185B; senescing to Brown Group 182C. Shape — Flat. Texture — Smooth.

Leaves:

*Arrangement.*—Imparipinnate compound leaves; mature axillary leaves consisting of 7 leaflets.

*Attachment.*—Petiolate.

*Dimensions.*—170 mm long and 110 mm wide.

*Abundance.*—Very abundant; approximately 150 leaves.

*Stipules.*—Size — 15 mm long and 5 mm wide. Stipule color — Yellow-Green Group 146C. Anthocyanin intonations — Very slight intonations of Greyed-Purple Group 184C are present on the adaxial surface of the midrib. Stipitate glands — A limited number of stipitate glands are present on the margins and abaxial leaf surface. Margins — Serrated, with a limited number of stipitate glands. Texture, adaxial surfaces — Leathery. Texture, abaxial surfaces — Leathery. Apex — Apiculate. Base — Flat; fused to the petiole.

*Petiole.*—Length — Average 10 mm. Diameter — Average 2.0 mm. Petiole color, adaxial surface — Yellow-Green Group 146D. Petiole color, abaxial surface — Yellow-Green Group 146C. Anthocyanin intonations — None. Margins — Regularly sequenced stipitate glands. Prickles — A single prickle is present on the abaxial surface. Stipitate glands — A limited number of stipitate glands are present on the margins and the abaxial surface. Texture — Glabrous. Strength — Strong.

*Rachis.*—Length — Average 20 mm. Diameter — Average 2.0 mm. Color — Yellow-Green Group 146D. Anthocyanin intonations — Slight intonations of Greyed-Red Group 182B are present at the point of leaf attachment on the adaxial surface and also along the margins. Margins — With stipitate glands. Prickles — A few small prickles on the abaxial surface. Stipitate glands — An abundance of stipitate glands are present along the margins and the abaxial surface. Texture — Glabrous.

*Leaflets.*—Dimensions — Average size of the terminal leaflet is 65 mm long and 35 mm wide. Shape — Ovate. Apex — Acute. Base — Obtuse. Margins — Serrated; slightly undulated. Luster, texture and pubescence; adaxial surface — Semi-glossy, smooth and glabrous. Luster, texture and pubescence; abaxial surface — Matte, rugose and glabrous. Juvenile foliage color, adaxial surface — Yellow-Green Group 147B. Juvenile foliage color, abaxial surface — Yellow-Green Group 147B. Mature foliage color, adaxial surface — Yellow-Green Group 147A. Mature foliage color, abaxial surface — Yellow-Green Group 147C. Anthocyanin intonations — Strong intonations of Greyed-Purple Group 187B are present at the apices of juvenile foliage; weaker intonations of Greyed-Purple Group 187B are present at the marginal zone and midrib of both surfaces of the juvenile foliage. Venation — Reticulate. Petiolule — Dimensions — 5 mm long and 1 mm in diameter. Petiolule color, adaxial surface — Yellow- Green Group 146B. Petiolule color, abaxial surface — Yellow-Green Group 146D. Anthocyanin intonations — None present. Prickles — None present. Texture, adaxial and abaxial surfaces — Leathery. Margins — With stipitate glands on both the adaxial and abaxial surfaces.

Inflorescence:

*Inflorescence type.*—Panicles which bear 3 to 6 flower buds. Flowers are held upright to slightly pendant.

*Blooming habit.*—Recurrent; floriferous.

*Size.*—15 cm tall and 14 cm wide, on average.

*Peduncle.*—Length — 60 to 100 mm average length. Diameter — 3.0 to 4.0 mm average diameter. Color — Yellow-Green Group 146C. Anthocyanin intonations — Slight intonations of Greyed-Purple Group 183C are present on a portion of the peduncle. Strength — Strong. Surface — Smooth with stipitate glands and numerous prickles; prickle color is Greyed-Purple Group 184B.

Flowering laterals: Present below the initiation of inflorescence. Generally 1 to 2 flowering laterals are present, with 1 flower per flowering shoot.

Bud:

*Bud form.*—Short; pointed ovoid.

*Size.*—Upon opening, 30 mm in length from base of receptacle to distal end of bud and 23 mm diameter at its widest point.

*Texture.*—Smooth.

*Color, as sepals first unfold.*—Orange-Red Group 32C.

*Color when one-quarter open, inner side.*—Marginal zone — Orange Group 24C. Middle zone — Yellow Group 11D. Basal zone — Yellow Group 13B.

*Color when one-quarter open, outer side.*—Marginal zone — Red Group 37B. Middle zone — Red Group 37B, with center striped Yellow-White Group 158D. Basal zone — Yellow-Orange Group 14C, with a petal spot, Red Group 45C.

Flower:

*Pedicel.*—Length — 35 to 60 mm average length. Diameter — 2.0 to 3.0 mm average diameter. Color — Yellow-Green Group 146C. Anthocyanin intonations — Very strong intonations of Greyed-Purple Group 183C. Strength — Strong to somewhat strong. Surface — Glabrous with an abundance of stipitate glands.

*Calyx.*—General — Comprised of five polysepalous sepals, with weak to moderate foliaceous appendages present on two of the five sepals. Diameter of calyx — 80 mm, at anthesis.

*Sepals.*—Color, upper surface — Yellow-Green Group 146D. Color, lower surface — Yellow-Green Group 146B. Anthocyanin intonations — Strong intonations of Greyed-Purple Group 185B on the lower surface, and Greyed-Purple Group 185D on the upper surface. Size — 25 to 35 mm long and 7 to 8 mm wide, on average. Apex — Apiculate to cirrose; typically 1 to 2 sepals are cirrose. Base — Flat at union with receptacle. Quantity — Five.

*Upper surface.*—Lightly pubescent.

*Lower surface.*—Stipitate glands present.

*Margins.*—Pubescent with abundant stipitate glands.

*Corolla.*—Habit — Double. Density of petals — Medium. General shape of corolla — Irregular round. Profile of corolla when viewed from the side — Upon opening, upper portion — Flat. Upon opening, lower portion — Concave. Open flower, upper portion — Flattened convex. Open flower, lower portion — Flattened convex. Dimensions — Small size for a floribunda rose. When open, the average flower diameter is 70 mm and the average flower height is 40 mm. Fragrance — Light, sweet fragrance. Duration — On the plant for 3 to 4 days. Senesced petals drop away cleanly. Petals — Petal count — Exhibits double flowers with an average of 34 petals under normal conditions. Petal reflex — Petals are slightly reflexed. Timing of petal reflex — Simultaneous. Petal margin — Entire. Petal shape — Obovate. Apex — Obtuse. Base — Cuneate. Dimensions — 40 mm long and 35 mm wide. Texture, inner surface — Smooth. Texture, outer surface — Smooth. Petal color, upon opening — Outermost petals, inner surface — Marginal zone — Orange Group 24D. Middle zone — Orange Group 24D. Basal zone — Yellow Group 13B. Outermost petals, outer surface — Marginal zone — Red Group 38B. Middle zone — Orange-Red Group 32D. Basal zone — Yellow Group 9C. Innermost petals, inner surface — Marginal zone — Yellow-Orange Group 23B. Middle zone — Distinct stripe, Yellow Group 6B. Basal zone — Yellow Group 6B. Innermost petals, outer surface — Marginal zone — Red Group 41D. Middle zone — Distinct stripe, Yellow Group 6B. Basal zone — Yellow Group 6B. Basal petal spots, upon opening — Outermost petals — Color, inner surface — No distinct petal spot. Color, outer surface — Yellow Group 9C. Dimensions — 3 mm wide and 3 mm tall. Innermost petals — Color, inner surface — Yellow Group 6B. Color, outer surface — Yellow Group 6B. Dimensions — 3 mm wide and 3 mm tall. Petal color, after opening — Outermost petals, inner surface — Marginal zone — Yellow-Orange Group 20D. Middle zone — Yellow-Orange Group 20D. Basal zone — Yellow-Orange Group 20D. Outermost petals, outer surface — Marginal zone — Red Group 36D. Middle zone — Red Group 36D. Basal zone — Yellow Group 2B. Innermost petals, inner surface — Marginal zone — Yellow-Orange Group 20D. Middle zone — Yellow-Orange Group 20D. Basal zone — Yellow Group 5B. Innermost petals, outer surface — Marginal zone — Red Group 38D. Middle zone — Red Group 38D. Basal zone — Yellow Group 2B. Basal petal spots, after opening — Outermost petals — Color, inner surface — Yellow Group 8A. Color, outer surface — Yellow Group 5B. Dimensions — 2 mm wide and 2 mm tall. Innermost petals — Color, inner surface — Yellow Group 5B. Color, outer surface — Yellow Group 2B. Dimensions — 2 mm wide and 2 mm tall. General Tonality — On open flower, Orange Group 24D. No change in general tonality at the end of the fourth day; thereafter the general tonality is Orange Group 27D. Petaloids — Quantity — 3 petaloids per flower, on average. Dimensions — Approximately 2 to 5 mm long and 2 to 4 mm wide. Color, inner surface — Marginal zone — Yellow-Orange Group 20D. Middle zone — Yellow-Orange Group 20D. Basal zone — Yellow Group 12D. Color, outer surface — Marginal zone — Red Group 38B. Middle zone — Red Group 38B. Basal zone — Yellow Group 4B. Margins — Very irregular; entire to undulated to indented. Shape — Oval to obovate to spatulate. Apex — Obtuse. Base — Attenuate to obtuse. Texture, inner and outer surfaces — Smooth.

Reproductive organs:

*Stamens.*—Quantity — Approximately 68, on average, and regularly arranged around the styles. Anthers — Shape — Reniform. Dimensions — 3.0 mm long and 0.5 mm wide, on average. Color — Greyed-Orange Group 163A. Pollen — Present; scarce. Color is Greyed-Orange Group 165B. Filaments — Color — Yellow Gimp 12A. Length — 5 mm.

*Pistils.*—Quantity — Average; approximately 50. Stigmas — Size — 1 mm. Location — Slightly inferior in position to anthers. Color — Greyed-Yellow Group 162A. Styles — Length — Approximately 4 mm long. Color — Yellow-Green 145C.

*Ovary.*—Dimensions — 5 mm long and 4 mm in diameter. Color — White Group 155A.

*Receptacle.*—Shape — Funnel-shaped. Dimensions — Approximately 7 mm high and 7 mm wide. Color — Yellow-Green Group 146C, with very strong intonations of Greyed-Purple Group 187B present over approximately 90 percent of the receptacle. Texture — Smooth, with a few fine white hairs, colored nearest to White Group 155A.

Hips and seed formation: Not observed.

COMPARISONS WITH THE PARENTS

The new rose plant may be distinguished from its seed parent, *Rosa hybrida* 'INTERflocu', by the following combination of characteristics:

1. 'KORforst750' exhibits copper-yellow flowers, whereas 'INTERflocu' exhibits yellow flowers with pink edges.
2. 'KORforst750' exhibits high disease resistance, whereas 'INTERflocu' exhibits average disease resistance.
3. 'KORforst750' exhibits a small size flower for a floribunda rose, whereas 'INTERflocu' exhibits a large flower.

The new rose plant may be distinguished from its pollen parent, a *Rosa hybrida* breeding line developed by the inventor, by the following combination of characteristics:

1. 'KORforst750' exhibits copper-yellow flowers, whereas the pollen parent exhibits yellow flowers.
2. 'KORforst750' exhibits a double petal count, whereas the pollen parent exhibits a semi-double petal count.
3. 'KORforst750' exhibits a bushy growth habit, whereas the pollen parent exhibits an upright habit.

COMPARISON WITH THE MOST SIMILAR *ROSA* CULTIVAR KNOWN TO THE INVENTOR

For a comparison, several physical characteristics of the *Rosa hybrida* variety 'KORmelaus', a rose variety from the same inventor which is described and illustrated in U.S. Pat. No. 26,116, are compared to 'KORforst750' in Chart 1.

CHART 1

| Characteristic | 'KORforst750' | 'KORmelaus' |
|---|---|---|
| General tonality of the flower, at anthesis. | Orange Group 24D. | Yellow-Orange Group 29A. |
| Petal count. | 34 or more. | 23 to 30. |
| Anthocyanin intonations. | Strong intonations on the juvenile leaflets, leaflet midribs, and rachis; strong intonations on juvenile stems. | Weaker intonations on the juvenile leaflets, leaflet midribs, and rachis; weaker intonations on juvenile stems. |

That which is claimed is:

1. A new and distinct variety of rose plant named 'KORforst750', as described and illustrated herein.

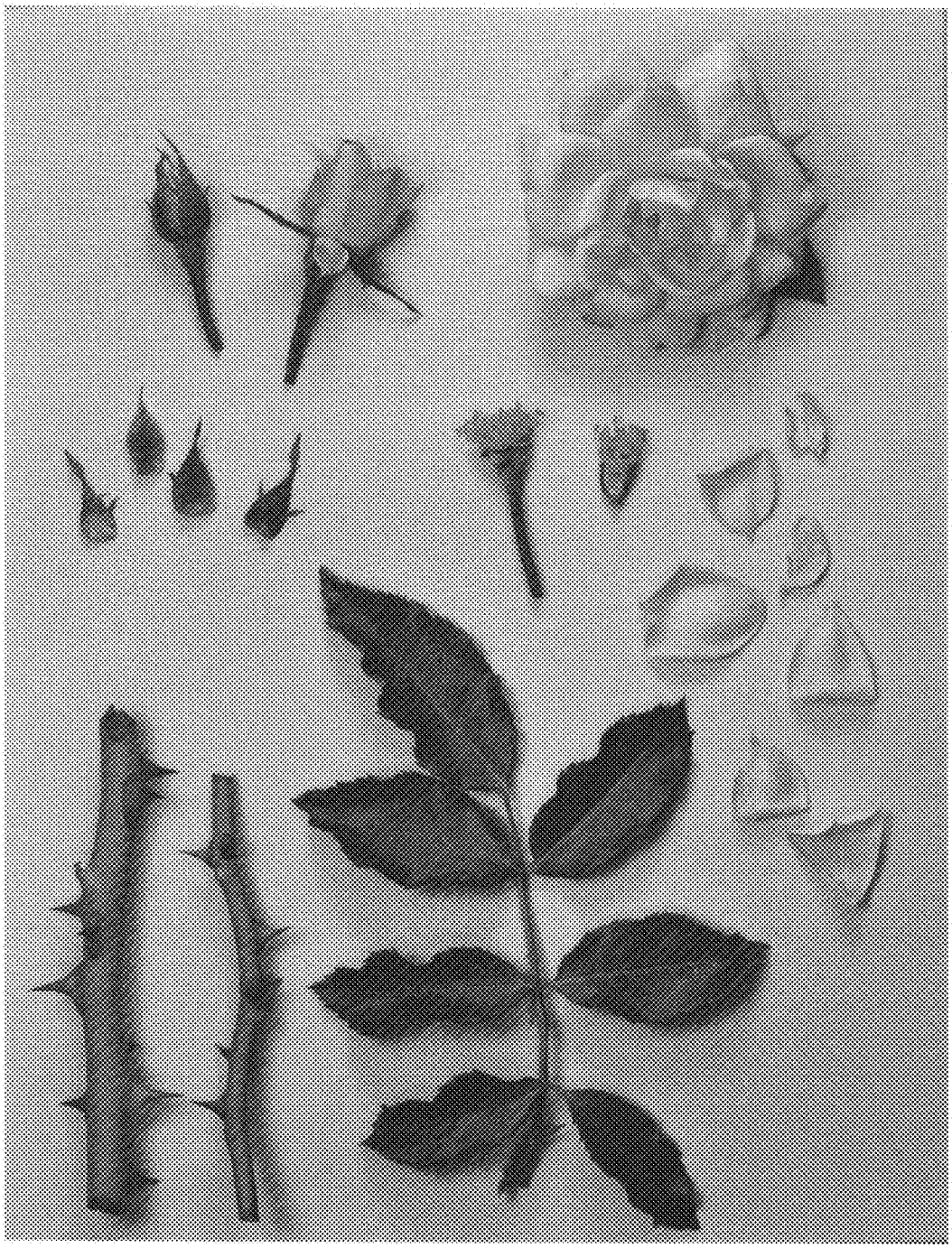

* * * * *